US007064192B2

(12) United States Patent
Randolph et al.

(10) Patent No.: US 7,064,192 B2
(45) Date of Patent: *Jun. 20, 2006

(54) HIGH PRESSURE REFOLDING OF PROTEIN AGGREGATES AND INCLUSION BODIES

(75) Inventors: Theodore W. Randolph, Niwot, CO (US); John F. Carpenter, Littleton, CO (US); Richard St. John, San Francisco, CA (US)

(73) Assignee: The Regents of the University of Colorado, Boulder, CO (US)

( * ) Notice: Subject to any disclaimer, the term of this patent is extended or adjusted under 35 U.S.C. 154(b) by 406 days.

This patent is subject to a terminal disclaimer.

(21) Appl. No.: 10/292,692

(22) Filed: Nov. 12, 2002

(65) Prior Publication Data

US 2003/0083475 A1    May 1, 2003

Related U.S. Application Data

(62) Division of application No. 09/350,327, filed on Jul. 9, 1999, now Pat. No. 6,489,450.

(60) Provisional application No. 60/350,327, filed on Jul. 9, 1999, provisional application No. 60/092,208, filed on Jul. 9, 1998.

(51) Int. Cl.
C07K 1/02 (2006.01)
C12N 9/00 (2006.01)
(52) U.S. Cl. ...................... 530/427; 435/183
(58) Field of Classification Search ............... 530/427; 435/183
See application file for complete search history.

(56) References Cited

U.S. PATENT DOCUMENTS

| 4,652,630 A | 3/1987 | Bentle et al. ............... 530/344 |
| 4,659,568 A | 4/1987 | Heilman, Jr. ............ 424/231.1 |
| 4,677,196 A | 6/1987 | Rausch et al. ............. 530/412 |
| 4,766,224 A | 8/1988 | Rausch |
| 4,923,967 A | 5/1990 | Bobbitt et al. ............. 530/351 |
| 4,929,700 A | 5/1990 | Halenbeck et al. |
| 4,985,544 A | 1/1991 | Yokoo et al. ............... 530/399 |
| 5,023,323 A | 6/1991 | Ho ............................. 530/399 |
| 5,064,943 A | 11/1991 | McCoy et al. ............. 530/399 |
| 5,077,392 A | 12/1991 | Rudolph et al. ......... 530/387.1 |
| 5,109,117 A | 4/1992 | Ho ............................. 530/399 |
| 5,162,507 A | 11/1992 | Wolfe et al. ............... 530/412 |
| 5,410,026 A | 4/1995 | Chang et al. .............. 530/408 |
| 5,593,865 A | 1/1997 | Rudolph et al. ........... 435/69.1 |
| 5,605,691 A | 2/1997 | Carroll ..................... 424/184.1 |
| 5,708,148 A | 1/1998 | Schmitz et al. |
| 5,714,371 A | 2/1998 | Ramanathan et al. ....... 435/219 |
| 5,728,804 A | 3/1998 | Sharma et al. ............. 530/350 |
| 6,489,450 B1 * | 12/2002 | Randolph et al. .......... 530/427 |
| 2004/0038333 A1 | 2/2004 | Randolph et al. |
| 2005/0020818 A1 | 1/2005 | Robinson et al. |

FOREIGN PATENT DOCUMENTS

WO    WO-00/02901 A1    1/2000

OTHER PUBLICATIONS

Betts, S. et al. (1997). "Mutational Effects Of Inclusion Body Formation," *In Advances in Protein Chemistry*, vol. 50, pp. 243-264.
Boteva, R. et al. (1996). "Dissociation Equilibrium Of Human Recombinant Interferon:γ," *Biochemistry* 35(47):14825-14830.
Clark, E.D.B. et al. (1999). "Inhibition Of Aggregation Side Reactions During In Vitro Protein Folding," *In Methods in Enzymology*, vol. 309, pp. 217-236.
Ealick, S.E. et al. (May 3, 1991). "Three-Dimensional Structure of Recombinant Human Interferon-γ," *Science* 252:698-702.
Ferráo-Gonzales, A.D. et al. (Jun. 6, 2000). "The Preaggregate State of an Amyloidogenic Protein: Hydrostatic Pressure Converts Native Transthyretin Into the Amylidogenic State," *PNAS USA* 97(12):6445-6450.
Fink, A.L. (Feb. 1, 1998). "Protein Aggregation: Folding Aggregates, Inclusion Bodies And Amyloid," *Folding & Design* 3(1):R9-R23.
Foguel, D. et al. (Jun. 5, 1999). "Hydrostatic Pressure Rescues Native Protein from Aggregates," *Biotechnology and Bioengineering* 63(5):552-558.
Gross, M. et al. (1994). "Proteins Under Pressure—The Influence Of High Hydrostatic-Pressure on Structure, Function and Assembly of Proteins and Protein Complexes," *European Journal of Biochemistry* 221(2):617-630.
Kendrick, B.S. et al. (Oct. 1997). "Preferential Exclusion of Sucrose From Recombinant Interleukin-1 Receptor Antagonist: Role in Restricted Conformational Mobility and Compaction of Native State," *Proc. Natl. Acad. Sci. USA* 94:11917-11922.

(Continued)

Primary Examiner—Jean C. Witz
Assistant Examiner—Susan Hanley
(74) Attorney, Agent, or Firm—Morrison & Foerster LLP

(57) ABSTRACT

The present disclosure provides an effective method for the refolding of denatured proteins in solution so that properly folded, biologically active protein in solution is recovered in high yield. The refolding takes place at pressures between about 0.25 kbar to about 3.5 kbar, advantageously at about 1.5 kbar to about 3 kbar. Typically a chaotropic agent is present at a concentration which is not effective for denaturing protein at atmospheric pressure, and optionally, oxidation-reduction reagents can be incorporated in the refolding solution so that native intramolecular disulfide bonds can be formed where that is desired. The method is applicable to substantially all proteins, especially after solubilization and/or denaturation of insoluble protein aggregates, inclusion bodies, or abnormal oligomeric (soluble) aggregates.

17 Claims, 6 Drawing Sheets

OTHER PUBLICATIONS

Kendrick, B.S. et al. (Nov. 1998). "A Transient Expansion of the Native State Precedes Aggregation of Recombinant Human Interferon-γ," *Proc. Natl. Acad. Sci. USA* 95(24):14142-14146.

Masson, P. et al. (2001). "High-Pressure Biotechnology in Medicine and Pharmaceutical Science," *Journal of Biomedicine and Biotechnology* 1(2):85-88.

Panda, M. et al. (Jan. 7, 2000). "Productive and Nonproductive Intermediates in the Folding of Denatured Rhodanese," *Journal of Biological Chemistry* 275(1):63-70.

Silva, J.L. et al. (1993). "Pressure Stability of Proteins," *Annual Review of Physical Chemistry*, 44:89-113.

Silva, J.L. et al. (Sep. 25, 1989). "Anomalous Pressure Dissociation Of Large Protein Aggregates—Lack Of Concentration Dependance And Irreversibility At Extreme Degrees Of Dissociation Of Extracellular Hemoglobin," *J. Biol. Chem.* 264(27):15863-15868.

St. John, R.J. et al. (Nov. 9, 1999). "High Pressure Fosters Protein Refolding From Aggregates At High Concentrations," *Proc. Natl. Acad. Sci., USA*, 96(23):13029-13033.

St. John, R.J. et al. (Dec. 14, 2001). "High Pressure Refolding of Recombinant Human Growth Hormone from Insoluble Aggregates," *Journal of Biological Chemistry* 276(50):46856-46863.

Webb, J.N. et al. (Jun. 19, 2001). "Partial Molar Volume, Surface Area, and Hydration Changes for Equilibrium Unfolding and Formation of Aggregation Transition State: High-Pressure and Cosolute Studies on Recombinant Human IFN-γ," *PNAS* 98(13):7259-7264.

Anfinsen, "Principals that govern the folding of protein chains," *Science*, 181(4096):223-230, 1973.

Bam et al., "Molten globule intermediate of recombinant human growth hormone: stabilization with surfactants," *Biotechnology Progress*, 12:801-809, 1996.

Bam et al., "Tween protects recombinant human growth hormone against agitation-induced damage via hydrophobic interactions" *Journal of Pharmaceutical Sciences*, 87:1554-1559, 1998.

Bowden et al., "Structure and morphology of protein inclusion bodies in Escherichia coli," *Bio/Technology*, 9:725-730, 1991.

Carpenter et al., "Rational design of stable lyophilized protein formulations: some practical advice," *Pharmaceutical Research*, 14:969-975, 1997.

Clark et al., "Oxidative renaturation of hen egg-white lysozyme. Folding vs. aggregation," *Biotechnology Progress*, 14:47-54, 1998.

Da Poian et al., "Differences in pressure stability of the three components of cowpea mosaic virus: implications for virus assembly and disassembly," *Biochemistry*, 33:8339-8346, 1994.

Defaye et al., "Renaturation of metmyoglobin subjected to high isostatic pressure," *Food Chemistry*, 52:19-22, 1995.

DeLoskey et al., "Isolation and refolding of H-ras from inclusion bodies of Escherichia coli: refold procedure and comparison of refolded and soluble H-ras," *Archives of Biochemistry and Biophysics*, 311:72-78, 1994.

Dewa et al., "Compression refolding of cytochrome C," *Protein and Peptide Letters*, 5:265-268, 1998.

Fischer et al., "A novel sequential procedure to enhance the renaturation of recombinant protein from Escherichia coli inclusion bodies," *Protein Engineering*, 5:593-596, 1992.

Fischer, In: *Lysozymes: Model Enzymes in Biochemistry and Biology*, Jolles(ed.), Birkhauser-Verlag, Boston, pp. 143-161, 1996.

Goldberg and Creighton, "Energetics of protein structure and folding," *Biopolymers*, 24:167-182, 1985.

Goldberg et al., "A kinetic study of the competition between renaturation and aggregation during the refolding of denatured-reduced egg white lysozyme," *Biochemistry*, 30:2790-2797, 1991.

Gorovits and Horowitz, "High hydrostatic pressure can reverse aggregation of protein folding intermediates and facilitate acquisition of native structure," *Biochemistry*, 37:6132-6135, 1998.

Gorovits et al., "High hydrostatic pressure induces the dissociation of cpn60 tetradecamers and reveals a plasticity of monomers," *The Journal of Biological Chemistry*, 5:2061-2066, 1995.

Heremans and Smeller, "Protein structure and dynamics at high pressure," *Biochimica et Biophysica Acta*, 1386:353-370, 1998.

Hevehan and Clark, "Oxidative renaturation of hysozyme at high concentrations," *Biotechnology and Bioengineering*, 54:221-230, 1997.

Jaenicke and Koberstein, "High pressure dissociation of lactic dehydrogenase," *FEBS Letters*, 17:351-354, 1971.

Kornblatt et al., "The pressure-induced, reversible inactivation of mouse brain enolases," *Eur. J. Biochem.*, 128:577-581, 1982.

Lange et al., "Pressure induced protein structural changes as sensed by $4^{th}$ derivative UV spectroscopy," *Progress in Biotechnology*, 13:135-140, 1996.

Leach and Scheraga, "Effect of light scattering on ultraviolet difference spectra," *Journal of the American Chemical Society*, 82:4790-4792, 1960.

Maachipalli-Reddy et al., "Effect of inclusion body contaminants on the oxidative renaturation of hen egg white lysozyme," *Biotechnology Progress*, 13-144,150, 1997.

Maeda et al., "Effective renaturation of denatured and reduced immunoglobulin G in vitro without assistance of chaperone," *Protein Engineering*, 9:95-100, 1996.

Mitraki and King, "Protein folding intermediates and inclusion body formation," *Bio/Technology*, 7:690-697, 1989.

Mitraki et al., "Quasi-irreversibility in the unfolding-refolding transition of phosphoglycerate kinase induced by guanidine hydrochloride," *European Journal of Biochemistry*, 163:29-34, 1987.

Moore and Leppert, "Role of aggregated human growth hormone (hGH) in development of antibodies to hGH," *Journal of Clinical Endocrinology and Metabolism*, 51:691-697, 1980.

Müller et al., "Thermodynamics and mechanism of high-pressure deactivation and dissociation of porcine lactic dehydrogenase," *Biophysical Chemistry*, 16:1-7, 1982.

Oberg et al., "Nativelike secondary structure in interleukin-1β inclusion bodies by attenuated total reflectance FTIR," *Biochemistry*, 33:2628-2634, 1994.

Onuchic et al., "Theory of protein folding," *Ann. Rev. Phys. Chem.*, 48:545-600, 1997.

Paladini and Weber, "Pressure-induced reversible dissociation of onolase," *Biochemistry*, 20:2587-2593, 1981.

Panick et al., "Structural characterization of the pressure-denatured state and unfolding/refolding kinetics of staphylococcal nuclease by synchrotron small-angle X-ray scattering and Fourier-transform infrared spectroscopy," *J. Mol. Biol.*, 275:389-402, 1998.

Przybycien et al., "Secondary structure characterization of β-lactamase incinsion bodies," *Protein Engineering*, 7:131-136, 1994.

Ratner et al., "Persistent cutaneous insulin allergy resulting from high-moleuclar-weight insulin aggregates," *Diabetes*, 39-728-733, 1990.

Rietveld et al., "Deterministic pressure dissociation and unfolding of triose phosphate isomerase:persistent heterogeneity of a protein dimer," *Biochemistry*, 35:7743-7751, 1996.

Ruan and Weber, "Dissociation of yeast hexokinase by hydrostatic pressure," *Biochemistry*, 27:3295-3301, 1988.

Rudolph and Lilie, "*In vitro* folding of inclusion body proteins," *The FASEB Journal*, 10:49-56, 1996.

Rudolph, "Renaturation of recombinant, disulfide-bonded proteins form 'inclusion bodies'," In: *Modern Methods in Protein and Nucleic Acid Research*, Tschesche (ed.), pp. 149-171, 1990.

Shortle, "The denatured state (the other half of the folding equation) and its role in protein stability," *FASEB*, 10:27-34, 1996.

Silva et al., "10. Pressure and cold denaturation of proteins, protein-DNA complexes, and viruses," In: *High-Pressure Effects in Molecular Biophysics and Enzymology*, Markley et al. (eds.), Oxford University Press, pp. 133-148, 1996.

Smeller et al., "Pressure effect on the temperature-induced unfolding and tendency to aggregate of myoglobin," *Biochemistry*, 38:3816-3820, 1999.

Spolar et al., "Coupling of local folding to site-specific binding of proteins to DNA," *Science*, 263:777-784, 1994.

Tang and Ruan, "Pressure-induced dissociation of beef liver L-glumate dehydrogenase," *Progress in Biotechnology*, 13:163-166, 1996.

Thornton and Ballow, "Safety of intravenous immunoglobulin," *Archives of Neurology*, 50:135-136, 1993.

Valax and Georgiou, "Molecular characterization of β-lactamase inclusion bodies produced in *Escherichi coli* 1. Composition," *Biotechnology Progress*, 9:539-547, 1993.

Vandenbroeck et al., "Refolding and single-step purification of porcine interferon-γ from *Escherichia coli* inclusion bodies," *European Journal of Biochemistry*, 215:481-486, 1993.

Weber, "Dissociation of oligomeric proteins by hydrostatic pressure," In: *High Pressure Chemistry and Biochemistry*, van Eldik and Jonas, (eds.), pp. 401-420, 1987.

Yamaguchi et al., "High pressure NMR study of protein unfolding," *Progress in Biotechnology*, 13:141-146, 1996.

Zong et al., "High-pressure-assisted reconstitution of recombinant chloroperoxidase," *Biochemistry*, 34:12420-12425, 1995.

\* cited by examiner

HIGH PRESSURE REFOLDING OF PROTEIN AGGREGATES AND INCLUSION BODIES

CROSS REFERENCE TO RELATED APPLICATIONS

This is a divisional of application Ser. No. 09/350,327 filed Jul. 9, 1999, now U.S. Pat. No. 6,489,450, which claims priority to U.S. Provisional Application Ser. No. 60/350,327, filed Jul. 9, 1998.

This application claims benefit of U.S. Provisional Application No. 60/092,208, filed Jul. 9, 1998, which is incorporated by reference herein to the extent that it is consistent with the present disclosure.

ACKNOWLEDGMENT OF FEDERAL RESEARCH SUPPORT

Not Applicable

BACKGROUND OF THE INVENTION

The field of the present invention is protein biochemistry, in particular, the refolding of biologically active protein after dissolution of aggregated protein, which is often composed of denatured protein. In the present invention, refolding of such protein is carried out at relatively high pressures, relatively high protein concentration and desirably, in the presence of a relatively low concentration of at least one denaturant.

Existing methods for solubilizing and refolding protein aggregates and inclusion bodies into their native structure are discussed below. These methods include general processes and those developed for particular proteins. General processes are said to be useful for any protein aggregate, while "specific" methods work for a single case, and effectiveness is not claimed other proteins.

All of the general processes described below utilize strong denaturing agents such as sodium dodecyl sulfate (SDS), urea, or guanidine hydrochloride followed by a dilution or dialysis step. These processes require large amounts of potentially hazardous chemicals and large volumes with dilution. With the combination of pressure, as taught by the instant invention, the amount of denaturing chemicals used are reduced by a factor of 10 or even eliminated. In addition, because the present process can operate at relatively high protein concentrations, the dilution step is no longer necessary.

U.S. Pat. No. 5,077,392 (1991) describes a process for activation of recombinant protein produced in prokaryotes, in which the aggregated proteins are dissolved in 4–8M guanidine hydrochloride or 6–10M urea. Once solubilized, the buffer is dialyzed to a pH between 1 and 4. Finally, the solution is diluted to provide a nondenaturing and oxidizing environment to allow for refolding.

U.S. Pat. No. 5,593,865 (1997) describes a process for activating recombinant disulfide bond-containing eukaryotic proteins after expression in prokaryote hosts. Inclusion body proteins are dissolved in a strong denaturing agent (6M guanidine hydrochloride) containing reducing agents. In the refolding step, proteins are introduced into an environment which is oxidizing and nondenaturing.

U.S. Pat. No. 4,677,196 (1987) also describes purification and production of biologically active proteins from insoluble inclusion bodies. This is a general method for recovering proteins from insoluble form includes dissolving the protein aggregates in SDS. Once dissolved, the protein solution is separated from SDS by column chromatography. In the absence of SDS, the protein can refold. Finally, the protein is eluted from the column. Urea has also been included in dissolved protein solutions. After anion exchange chromatography, the urea from the refolded protein solution is removed by dialysis.

U.S. Pat. No. 5,605,691 (1997) describes solubilization of inclusion body proteins using SDS and heat. Once in solution, proteins are refolded by first diluting the SDS and then dialyzing away the SDS to nondenaturing concentrations.

U.S. Pat. No. 4,659,568 (1997) describes a process for solubilization, purification and characterization of protein from insoluble protein aggregates or complexes and compositions of matter therefrom. The insoluble protein aggregates or inclusion bodies are layered on top of a urea step gradient (3M to 7M urea). As the samples are centrifuged, the aggregates move through the gradient until they dissolve. This method provides a means of determining the urea concentration at which the protein dissolves.

U.S. Pat. No. 5,728,804 (1995) describes a process in which denatured or aggregated proteins are suspended in a detergent-free aqueous medium containing 5–7 M guanidine hydrochloride and incubated overnight. Once suspended, the sample is contacted with sufficient cyclodextrin to assist in the refolding of the proteins. Finally, the cyclodextrin is removed by dialysis.

Turning now to patents for processes developed for particular proteins, U.S. Pat. No. 4,652,630 (1987) describes a method for producing active somatotropin. In this method, the aggregates or inclusion bodies are solubilized in a chaotrope (3M to 5M urea), and the pH is adjusted to allow complete solubilization. Then the conditions are modified to allow oxidation in the presence of a nondenaturing concentration of chaotrope.

U.S. Pat. No. 5,064,943 (1991) also describes a method for solubilizing and renaturing somatotropin, but it does not require the use of a chaotrope. Here, the pH is adjusted to between 11.5 and 12.5 and maintained for 5 to 12 hours. Under these conditions, somatotropin will solubilize and renature.

U.S. Pat. No. 5,023,323 (1991) describes a process for naturation of somatotropin (growth hormone) aggregates in which the aggregates are dissolved in a denaturing chaotrope (1M to 8M urea). The solubilization step is followed by exposing the sample to an oxidizing environment in the presence of a nondenaturing concentration of chaotrope.

U.S. Pat. No. 5,109,117 (1992) describes a method in which somatotropin aggregates are dissolved in the presence of an organic alcohol and chaotrope (1M to 8M urea). Then the solubilized proteins are renatured in a nondenaturing, oxidizing environment.

U.S. Pat. No. 5,714,371 (1998) provides a method for refolding aggregates of hepatitis C virus protease. Aggregates are solubilized in 5M guanidine hydrochloride. Second, a reducing agent is added to the solution, and the pH is adjusted to provide an acidic pH. Third, the denaturing agent is removed from the solution by dialysis, and finally the pH is raised to its starting point.

U.S. Pat. No. 4,923,967 (1990) describes a process specific for human interleukin-2. Protein aggregates are dissolved in 4–8M guanidine hydrochloride with a sulfitolyzing agent. Once the proteins are dissolved, the sulfitolyzing agent is removed by solvent exchange. Finally, the temperature is raised to precipitate out interleukin-2 in pure form. To allow refolding, precipitates are dissolved again in guanidine hydrochloride plus a reducing agent. Finally, the solution is diluted to refold proteins.

U.S. Pat. No. 5,162,507 (1992) describes a process for recovering purified, oxidized, renatured recombinant interleukin-2 from microorganisms. Insoluble interleukin-2 isolated from microorganisms is solubilized in 2M to 4M guanidine hydrochloride. The guanidine hydrochloride solution is then diluted until the proteins precipitate out of the solution. The precipitates are then redissolved in a guanidine hydrochloride solution. The proteins are then oxidized to reform native disulfide bonds. Finally, the solution is diluted and interleukin-2 remains in solution.

U.S. Pat. No. 4,985,544 (1991) describes a process for renaturing fish growth hormone. In this process, the aggregates or inclusion bodies are dissolved using guanidine, urea, SDS, acid or alkali. The reducing agent is then removed, and an oxidizing agent is added. Finally, the denaturing agent is removed to allow refolding.

U.S. Pat. No. 5,410,026 (1995) describes a method in which insoluble, misfolded insulin-like growth factor-1 (IGF-1) is refolded into an active conformation. Once IGF-1 is isolated, it is incubated with 1–3M urea or 1M guanidine hydrochloride until the aggregates are solubilized and refolded.

Other U.S. patents of interest include U.S. Pat. Nos. 5,708,148; 4,929,700 and 4,766,224.

Because management and disposal of biotechnological processing materials are time-consuming and costly, because protein aggregates and denatured proteins in pharmaceutical preparations are inefficacious and dangerous, and because poor yields of biologically active protein harms the economics of recombinant protein production, there is a longfelt need in the art for a process for the efficient preparation of properly fold, non-aggregated and fully active protein, especially that expressed by recombinant means.

SUMMARY OF THE INVENTION

The present invention provides methods for recovering a properly folded, biologically active protein from mixtures containing aggregates or inclusion bodies containing the protein, or from solutions containing the protein in a denatured state. Proteins in solution, even highly purified proteins, can form aggregates with themselves or with other proteins, upon storage, or during production processes that involve fluid transfers, contact with surfaces or by other non-specific causes. Such aggregation can lead to loss of biological activity and can be harmful in therapeutic uses. The methods of the present invention result in disaggregation of aggregates present in mixtures of aggregated and native protein, and in renaturation of denatured protein in solution.

The processes of the invention are applied to solutions or mixtures where total protein concentration is in the range of from about 0.001 mg/ml to about 500 mg/ml, preferably from about 0.1 mg/ml to about 25 mg/ml and most preferably from about 1 mg/ml to about 10 mg/ml. Optionally in the embodiment of the invention used to disaggregate a protein and depending upon the protein to be disaggregated, a chaotropic agent can be added to the protein mixture. However, the concentration of chaotropic agent is limited to that which permits retention of biological activity of the protein in its native form. As will be understood in the art, the concentration of chaotropic agent, if any, will be selected according to the particular protein to be disaggregated, based upon its sensitivity to the chaotropic agent. With these limitations in view, the chaotropic agent can be present at concentrations in the range from 0 M to about 8 M, most often in the range from 0 M to about 1.0 M. The concentrations employed will also differ depending on the particular chaotropic agent employed.

An important feature of the invention is the application of elevated pressure to the mixture to be disaggregated. Elevated pressure is applied in two stages, first to accomplish disaggregation, where the pressure to be applied ranges from about 0.25 kbar to about 12 kbar for a time sufficient for disaggregation to occur. The pressure to be applied is chosen with regard to the particular protein to be disaggregated. A second stage of incubation at elevated pressure is carried out to permit re-folding of the protein to its native, biologically active (at atmospheric pressure) conformation. Surprisingly, incubation of disaggregated or denatured protein at elevated pressure in the range from 0.25 kbar to about 3.3 kbar promotes reconstitution of the native, biologically active (at atmospheric pressure) protein, even though higher pressures promote denaturation. Preferably the incubation pressure for renaturation is in the range from about 2 kbar to about 3.3 kbar. The optimum pressure for renaturation depends on the individual protein to be treated, as will be understood in the art.

An oxidizing agent and a reducing agent can be optionally included in the renaturation solution, for example, dithiothreitol, in the concentration range from about 1 mM to about 50 mM, and reduced glutathione, in the concentration range from about 1 mM to 50 mM. The pressure of such redox reagents provides that disulfide bonds are both readily formed and reduced. The mixtures for disaggregating or renaturing protein can also comprise surfactants, non-specific protein stabilizing agents, buffering agents, ligands of the protein being refolded, and the like.

Another embodiment of the invention, also employs pressure-facilitated refolding of denatured protein. In this embodiment, denatured protein in solution is provided in the presence of denaturing amounts of a chaotropic agent. The protein concentration in solution is in the range from about 0.001 mg/ml to about 500 mg/ml, preferably from about 0.1 mg/ml to about 25 mg/ml, more preferably from about 1 mg/ml to about 10 mg/ml. The chaotropic agent ranges in concentration from about 2 M to about 8 M, depending upon the protein to be denatured and the chaotropic agent. The denatured protein solution is incubated at elevated pressure in the pressure range effective for facilitating renaturation, namely from about 0.25 kbar to about 3.3 kbar and preferably from about 2 kbar to about 3.3 kbar. While under pressure, the concentration of chaotropic agent is reduced by any suitable means, for example, by dilution or by dialysis, to a level sufficient to permit biological activity of the protein at atmospheric pressure. Incubation takes place for a time sufficient to permit re-folding of the protein which usually occurs within 24 hours, depending on the protein. At the end of the pressure incubation period, the pressure is reduced to atmospheric pressure. In both embodiments of the invention, redox agents, stability agents, surfactants and the like can be added to the solution as described, supra.

The processes of the invention can be carried out at any temperature between the freezing point of the aqueous medium (about 0° C.) and the temperature at which biological activity is lost due to thermal denaturation. The upper limit will be somewhat different for each individual protein and will also be affected by the composition of the medium, pH, presence of stabilizing compounds and the like, as is known in the art. The preferred temperature for carrying out the process of the invention is within 20° C. of the upper limit temperature. For the disaggregation of growth hormone, see Example 4, disaggregation and renaturation occurred more rapidly at 60° C. (upper limit 80° C.) than at room temperature.

DETAILED DESCRIPTION OF THE INVENTION

Figure 1:
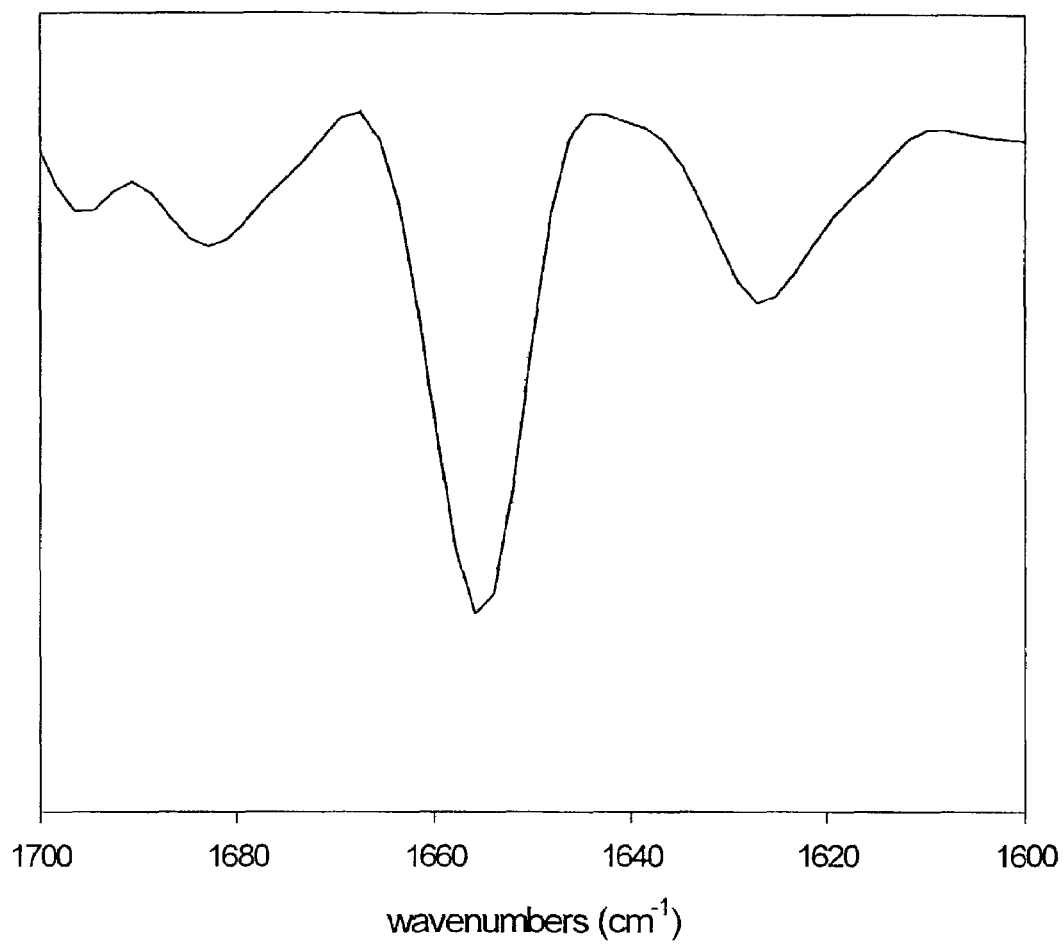
FIG. 1 shows the second derivative FTIR spectra of native recombinant human growth hormone (dashed line), and aggregated growth hormone (solid line). Spectra for native and aggregated protein samples were collected and processed as described in the Examples hereinbelow.

As used herein, a protein aggregate is composed of a multiplicity of protein molecules wherein noncovalent interactions and/or intermolecular disulfide bonds hold the protein molecules together. Typically, but not always, an aggregate contains sufficient molecules so that it is insoluble. There are also abnormal oligomeric proteins which occur in aggregates in solution. In addition, there is typically (but not always) a display of at least one epitope or region on the aggregate surface which is not displayed on the surface of native, non-aggregated protein. Inclusion bodies are a type of aggregate of particular interest, to which the present invention is applicable.

Native conformation of a protein, in the present context, refers to the secondary, tertiary and quaternary structures of a protein as it occurs in nature in its fully active state.

Biological activity of a protein as used herein, means at least 10% of maximal known specific activity as measured in an assay that is generally accepted in the art to be correlated with the known or intended utility of the protein. For proteins intended for therapeutic use, the assay of choice is one accepted by a regulatory agency to which data on safety and efficacy of the protein must be submitted. A protein having greater than 10% of maximal known specific activity is "biologically active" for the purposes of the invention.

Denatured as applied to a protein in the present context, means that native secondary and tertiary structure is disrupted to an extent that the protein does not have biological activity.

Refolding (renaturing, naturing), in the present context, means that a fully or partially denatured protein adopts secondary, tertiary and quaternary structure like that of the cognate native molecule. A (properly) refolded protein has biological activity which is substantially that of the non-denatured molecule. Where the native protein has disulfide bonds, oxidation to form native intramolecular disulfide bonds is a desired component of the refolding process.

Atmospheric pressure (ambient) is approximately 15 pounds per square inch (psi) or 1 bar.

Heterologous proteins are proteins which are normally not produced by a particular host cell. Recombinant DNA technology has permitted the expression of relatively large amounts of heterologous proteins (for example, growth hormone) from transformed host cells such as $E.\ coli$. These proteins are often sequestered in insoluble inclusion bodies in the cytoplasm and/or periplasm of the host cell. The inclusion bodies or cytoplasmic aggregates contain, at least in part, the heterologous protein to be recovered. These aggregates often appear as bright spots under a phase contrast microscope.

By host cell is meant a microbial cell such as bacteria and yeast or other suitable cell including animal or a plant cell which has been transformed to express the heterologous protein of interest. Host cells which are contemplated by the present invention are those in which the heterologous protein expressed by the cell is sequestered in refractile bodies. An exemplary host cell is $E.\ coli$ K12, strain W311OG [pBGHI], which has been transformed to effect expression of the desired heterologous protein.

A chaotropic agent is a compound, including, without limitation, guanidine hydrochloride (guanidinium hydrochloride, GdmHCl), sodium thiocyanate, urea and/or a detergent which disrupts the noncovalent intermolecular bonding within the protein, permitting the amino acid chain to assume a substantially random conformation.

A surfactant is a surface active compound which reduces the surface tension of water and includes, nonionic (including, but not limited to, t-octylphenoxypolyethoxy-ethanol and polyoxyethylene sorbitan), anionic (e.g., sodium dodecyl sulfate) and cationic (e.g., cetylpyridinium chloride) and amphoteric agents. Suitable surfactants include, but are not limited to deoxycholate, sodium octyl sulfate, sodium tetradecyl sulfate, polyoxyethylene ethers, sodium cholate, octylthioglucopyranoside, n-octylglucopyranoside, alkyltrimethylammonium bromides, alkyltrimethyl ammonium chlorides, sodium bis (2-ethylhexyl) sulfosuccinate.

Non-specific protein stabilizing agents include, but are not limited to, sucrose, trehalose, glycerol, betaine, amino acid(s), and trimethylamine oxide. A non-specific stabilizing agent generally acts to favor the most compact conformation of a protein.

Buffering agents are advantageously present in disaggregating and/or refolding mixtures to maintain a desired pH value or pH range. Inorganic buffer systems (phosphate, carbonate, among others) and organic buffer systems (citrate, Tris, MOPS, MES, HEPES, among others) are well known to the art.

A binding partner (or ligand) may be included in a refolding mixture. A binding partner is a compound which specifically binds (or otherwise interacts) with a target protein of interest. Ligands can include, without limitation, antibodies, receptors, peptides, peptidomimetics, vitamins, cofactors, prosthetic groups, substrates, products, competitive inhibitors, metals and other small or large molecules. The presence of such a binding partner is especially advantageous in a refolding mixture where that binding partner favors a native conformation of the target protein when it interacts with the refolding target protein.

Refractile bodies can be recovered using standard techniques as described, for example, in U.S. Pat. No. 4,652,630. For example, the host cell can be disrupted by mechanical means such as a Manton-Gaulin homogenizer or French press. It is preferred that the disruption process be conducted so that cellular debris from the host organism is so disrupted that it fails to sediment from the homogenate solution under low speed centrifugation sufficient to sediment the refractile bodies. The refractile bodies are preferably resuspended, washed and centrifuged again. The supernatant is discarded yielding a substantially pure preparation of refractile bodies. Although not critical to the practice of the present invention, it is preferred that the refractile body preparation be homogenized again to ensure a freely dispersed preparation devoid of agglomerated refractile bodies. The preparation may be homogenized in a Manton-Gaulin homogenizer at 3000–5000 psig.

It is known that heterologous proteins can be solubilized from refractile bodies of the host cell by subjecting the refractile bodies to an effective amount and concentration of guanidine hydrochloride, urea or other chaotropic agent, and a pH that depends on the particular protein to be solubilized. The concentration and absolute amount of chaotrope needed depends on the pH of the solution and on the amount and kind of protein to be solubilized.

In spite of recent progress in theoretical and computational approaches [Alm and Baker (1999) *Current Opinion in Structural Biology* 9:189–196 (1999); Berendsen, H. J. C. (1998) *Science* 282:642–643] to understanding protein folding and refolding, efforts to manipulate folding in vitro are often plagued by competing off-pathway aggregation processes. Protein aggregation is the subject of intense investigation in disciplines including human medicine, fundamental protein chemistry and biotechnology. For example, aggregation can have severe consequences in human diseases (e.g., Alzheimer's disease, and Parkinson's disease) [Lansbury, P. T., Jr. (1999) *Proc. Natl. Acad. Sci. USA* 96:3342–3344], and in the manufacturing, shipping, storage and delivery of protein therapeutics [Carpenter et al. (1997) *Pharmaceutical Research* 14:969–975].

In particular, exploitation of the unique medical benefits of recombinant protein therapeutics is often hindered by the formation of non-native protein aggregates from native protein molecules. Aggregation can occur during refolding, purification, concentration, vial filling, freeze-thawing, lyophilization/rehydration and delivery to patients. Particularly dramatic manifestations of the competition between proper folding pathways and off-pathway formation of non-native aggregates occur during attempts to obtain native recombinant proteins from precipitates formed during processing or inclusion bodies, both of which are essentially completely aggregated protein with substantial non-native structure [Mitraki and King (1989) *Bio/technology* 7:690–697; Bowden et al. (1991) *Bio/technology* 9:725–730; Przybycien et al. (1994) *Protein Engineering* 7:131–136; Oberg et al. (1994) *Biochemistry* 33:2628–2634]. If even a minor fraction (e.g., 1%) of a parenterally delivered protein is aggregated, adverse reactions including anaphylactic shock can be induced [Moore and Leppert (1980) *Journal of Clinical Endocrinology and Metabolism* 51:691–697; Ratner et al. (1990) *Diabetes* 39:728–733; Thornton and Ballow (1993) *Archives of Neurology* 50:135–136].

Currently, refolding proteins from non-native aggregates and inclusion bodies requires proteins to be disaggregated and then refolded into their native conformation. Most commonly, aggregates are solubilized in a strong chaotrope, such as 8M guanidine hydrochloride (GdmHCl) [Mitraki et al. (1987) *European Journal of Biochemistry* 163:29–34; Vandenbroeck et al. (1993) *European Journal of Biochemistry* 215:481–486; DeLoskey et al. (1994) *Archives of Biochemistry and Biophysics* 311:72–78; Rudolph and Lilie (1996) *The FASEB Journal* 10:49–56], which results in nearly complete unfolding of the protein molecules. Relatively high concentrations of urea or surfactant have also been used. Once soluble and unfolded, the proteins are first diluted with additional GdmHCl solution and then refolded by removing the chaotrope by dialysis or additional dilution. The refolding step, however, is very difficult and depends strongly on renaturing conditions [Valax and Georgiou (1993) *Biotechnology Progress* 9:539–547; Rudolph and Lilie (1996) supra]. For example, redox conditions, pH, rates of dialysis and protein concentration must all be empirically optimized for each protein [Rudolph, R. (1990) *Modern Methods in Protein and Nucleic Acid Research* (Tschesche, H. ed.) pp. 149–172]. Furthermore, because the process of protein folding is first order in protein concentration and the overall aggregation process is at least second order, aggregation is favored over refolding at higher protein concentrations. Hence, achieving acceptable yield (e.g., >10%) of refolded protein often requires protein to be refolded at very low concentrations (10–100 µg/mL) [Rudolph, R. (1990) supra; Goldberg et al. (1991) *Biochemistry* 30:2790–2797; Maachupalli-Reddy et al. (1997) *Biotechnology Progress* 13:144–150]. As a result, once a protein is refolded, it must be concentrated (typically 100- to 1000-fold) to final dosage concentration. Losses of native protein can also occur during this concentration step. In addition, yield of properly folded protein upon renaturation is often low regardless of refolding conditions. Finally, the large volumes of waste chaotrope solution generated are expensive to dispose of properly.

The present invention uses high pressure as an alternative to high concentrations of strong chaotropes for protein disaggregation and refolding. Pressures between 1 kbar and 3 kbar reversibly dissociate oligomeric proteins into subunits [Paladini and Weber (1981) *Biochemistry* 20:2587–2593; Muller et al. (1982) *Biophysical Chemistry* 16:1–7; Weber, G. (1987) *High Pressure Chemistry and Biochemistry* (R. van Eldik and J. Jonas eds.) pp. 401–420; Ruan and Weber (1988) *Biochemistry* 27:3295–3301]. Pressures above 4 kbar begin to denature the secondary structure of proteins [Lange et al. (1996) *Progress in Biotechnology* 13:135–140; Tang and Ruan (1996) *Progress in Biotechnology* 13:163–166; Yamaguchi et al. (1996) *Progress in Biotechnology* 13:141–146]. Although pressure has been shown to reduce aggregation rates during refolding from fully soluble, denatured protein [Gorovits and Horowitz (1998) *Biochemistry* 37:6132–6135], pressure is not believed to have been used as a tool to obtain native protein from abnormal oligomeric associates of protein, soluble aggregates, insoluble aggregates and inclusion bodies. Without wishing to be bound by theory, we believe that there is a "pressure window" where pressure is high enough to solubilize aggregates but still allows refolding to the native conformation. The model systems chosen were agitation-induced insoluble aggregates of recombinant human growth hormone, chaotrope-induced aggregates of hen egg white lysozyme containing non-native disulfides, and inclusion bodies containing β-lactamase produced in *Escherichia coli*.

Human growth hormone (rhGH) is a 22 kD protein formed into a four α-helical bundle. Its surface contains two relatively large regions with a high percentage of hydrophobic residues [de Vos et al. (1992) *Science* 255:306–312; Ultsch et al. (1994) *Journal of Molecular Biology* 236: 286–299]. Even gentle agitation of recombinant human growth hormone (rhGH) solutions results in aggregation and precipitation [Bam et al. (1998) *J. Pharm. Sci.* 87:1554–1559]. Upon agitation, 95% of the protein forms insoluble aggregates. To confirm that the structure of the precipitates is non-native, the secondary structure of rhGH aggregates was determined by infrared spectroscopy. Fourier Transform Infrared Spectroscopy (FTIR) was used to determine the secondary structure of growth hormone aggregates in solution. All spectra were collected on a Nicolet Magna model 550 spectrometer equipped with a dTGS detector. A 256-scan interferogram was acquired in single-beam mode with a 4 $cm^{-1}$ resolution. Aggregate slurries were placed in an adjustable path-length IR cell set at 8 microns. The same cell was used to collect a buffer blank (the buffer used for the blank was identical to the buffer in the aggregate slurry). Buffer and water vapor contributions were subtracted from the spectrum using the Nicolet software. Second derivative analysis was used for peak narrowing and resolution. Contributions from the second derivative of the water vapor spectrum were also subtracted from the spectrum. A seven-point smoothing was used to remove white noise, and baseline correction was performed over the amide I region. Finally, spectra were normalized by their total area over the amide I region. The second derivative spectra, in the conformationally-sensitive amide I region, of native and aggregated human growth hormone are given in FIG. 1. The spectrum of native rhGH is dominated by a strong band at 1654 $cm^{-1}$, which is due to high proportion of alpha helix [de Vos et al. (1992) *Science* 255:306–312; Ultsch et al. (1994) *Journal of Molecular Biology* 236: 286–299]. The spectrum for the aggregated protein shows a substantial absorbance at 1654 $cm^{-1}$, demonstrating partial retention of α-helix, and prominent non-native bands at 1627 $cm^{-1}$, and 1695 $cm^{-1}$. The latter bands are due to intermolecular β-sheet structure, a common structural motif in non-native protein aggregates, precipitates, fibrils, and inclusion bodies [Fink, A. L. (1998) *Folding and Design* 3:R9–R23].

The effect of pressure on disaggregation and refolding of rhGH was examined at protein concentrations between 0.87 and 8.7 mg/mL. Pressure was generated using high-pressure nitrogen (400 bar) connected to a 10-fold hydraulic intensifier equipment (High Pressure Equipment Company, Erie, Pa.). Samples were prepared in heat-sealed bulbs of SAMCO® transfer pipets, and placed in a to a 2 liter clover leaf reactor rated to 2,000 bar and filled with water. Samples were slowly pressurized (over 10 minutes) to final desired pressure to minimize pressurization-induced heating; the depressurization rate was approximately 10 bar per minute. Various concentrations of GdmHCl were tested on 0.87 mg/mL samples to determine whether chaotropes augment the effects of pressure. The range of GdmHCl tested (0–1M) was chosen so as to remain well below the concentrations where, at atmospheric pressure, rhGH begins to unfold or form molten globules [Bam et al. (1996) *Biotechnology Progress* 12:801–809]. At atmospheric pressure, unfolding is first detected at 3.5M GdmHCl. Thus, assuming that pressure (up to 2 kbar) does not greatly increase the effectiveness of GdmHCl as a denaturant, native rhGH is thermodynamically favored in the presence of the GdmHCl concentrations tested here.

Figure 2:
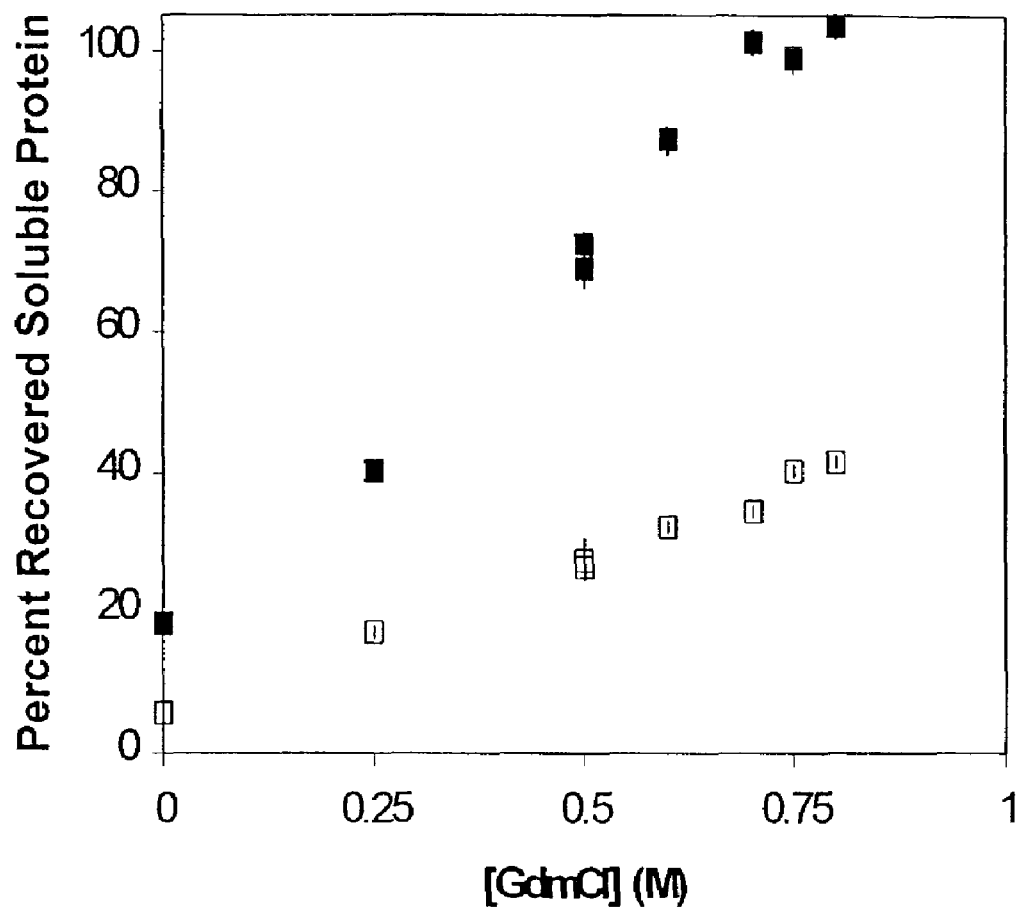
FIG. 2 is a plot of the percent recovered soluble rhGH as a function of GdmHCl concentration. Outlined points (□) represent atmospheric samples and solid points (■) represent samples pressurized to 2 kbar for 24 hours. In this and in the following figures, error bars represent +/−1 standard deviation, with data points taken at least in triplicate. Points with no apparent error bars have error bars smaller than the size of the data marker.

At atmospheric pressure and in the absence of GdmHCl, no protein refolding was detected (i.e., 95% of the protein remains aggregated) after 24 hours. Concentrations of soluble rhGH were determined by UV spectroscopy with extinction coefficients of 18,890 (cm mol/l)-1 at 278 nm (19) on a Hewlett Packard 8452A diode array spectrophotometer. Insoluble aggregates were removed by centrifugation (13,000 g, room temperature) for 15 minutes. Contributions due to soluble aggregates were subtracted from the signal as previously reported [Leach and Scheraga (1960) *Journal of the American Chemical Society* 82:4790–4792]. Even in the presence of up to 0.8M GdmHCl, control samples maintained at atmospheric pressure had at most 40% recovery of soluble protein (FIG. 2). In the absence of GdmHCl, pressurization to 2 kbar for 24 hours and return to atmospheric pressure increased soluble protein to 18% (FIG. 2). As the concentration of GdmHCl increased to 0.7M, the amount of soluble protein recovered after 24-hour incubation at 2 kbar increased to a maximum of 100%. The soluble protein was fully native based on examination of far- and near-UV circular dichroism spectra, documenting, respectively, that native secondary and tertiary structures were recovered. In addition, size exclusion chromatography documented that the soluble protein was monomeric.

Remarkably, high pressure refolding of rhGH appears to be independent of protein concentration. Once optimal refolding conditions were determined, we increased protein concentrations up to 8.7 mg/mL, orders of magnitude higher than conditions typically used for refolding studies. Samples pressurized for 24 hours at 2 kbar, 1 M GdmHCl also achieved 100% recovery of rhGH from aggregates.

These results document that neither pressure nor GdmHCl alone (<1M) is sufficient to allow 100% recovery of native, soluble rhGH. Furthermore, the effect of the combination of factors is synergistic, for reasons that are not clear at this point. However the current results show that, with pressure treatment, native rhGH can be recovered from aggregates using GdmHCl concentrations an order of magnitude lower, and at protein concentrations several orders of magnitude higher, than those typically used for refolding.

Figure 3A:
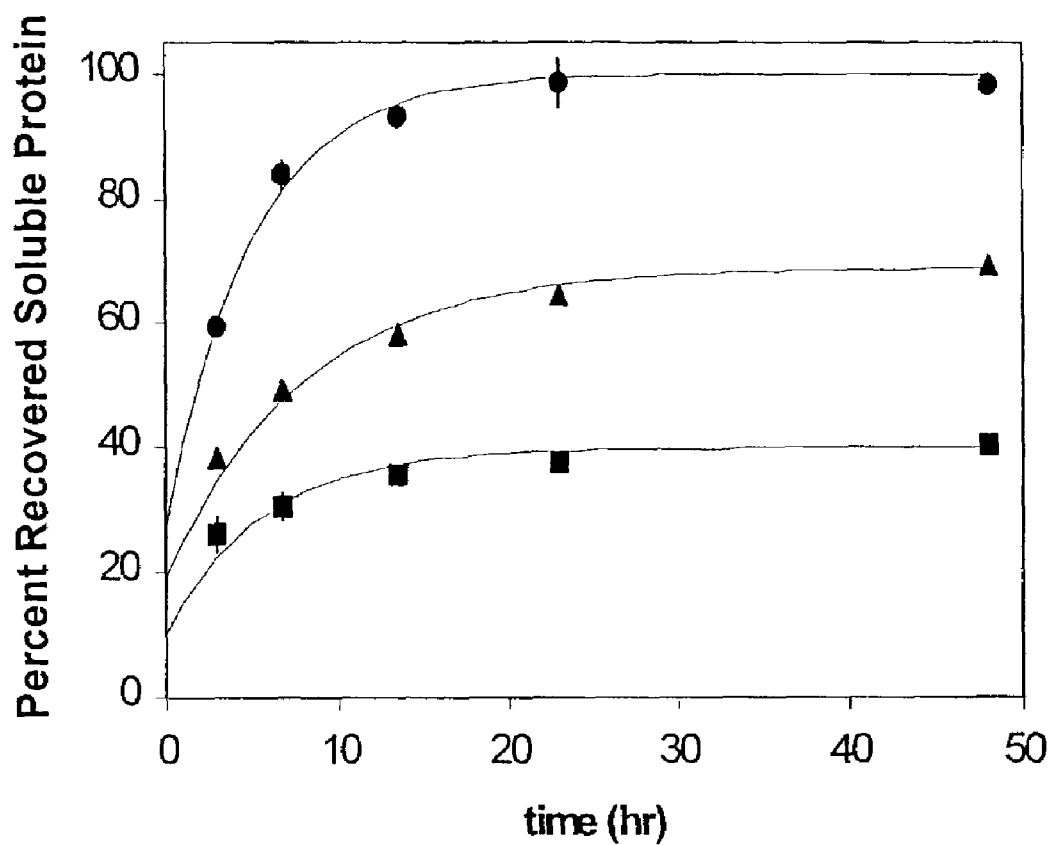
FIG. 3A graphically illustrates the percent recovered soluble rhGH as a function of time at 2 kbar. Squares (■) represent samples refolded in 0.25M GdmHCl, triangles (▲) represent samples refolded in 0.5M GdmHCl, and circles (●) represent samples refolded in 0.75M GdmHCl.
Figure 3B:
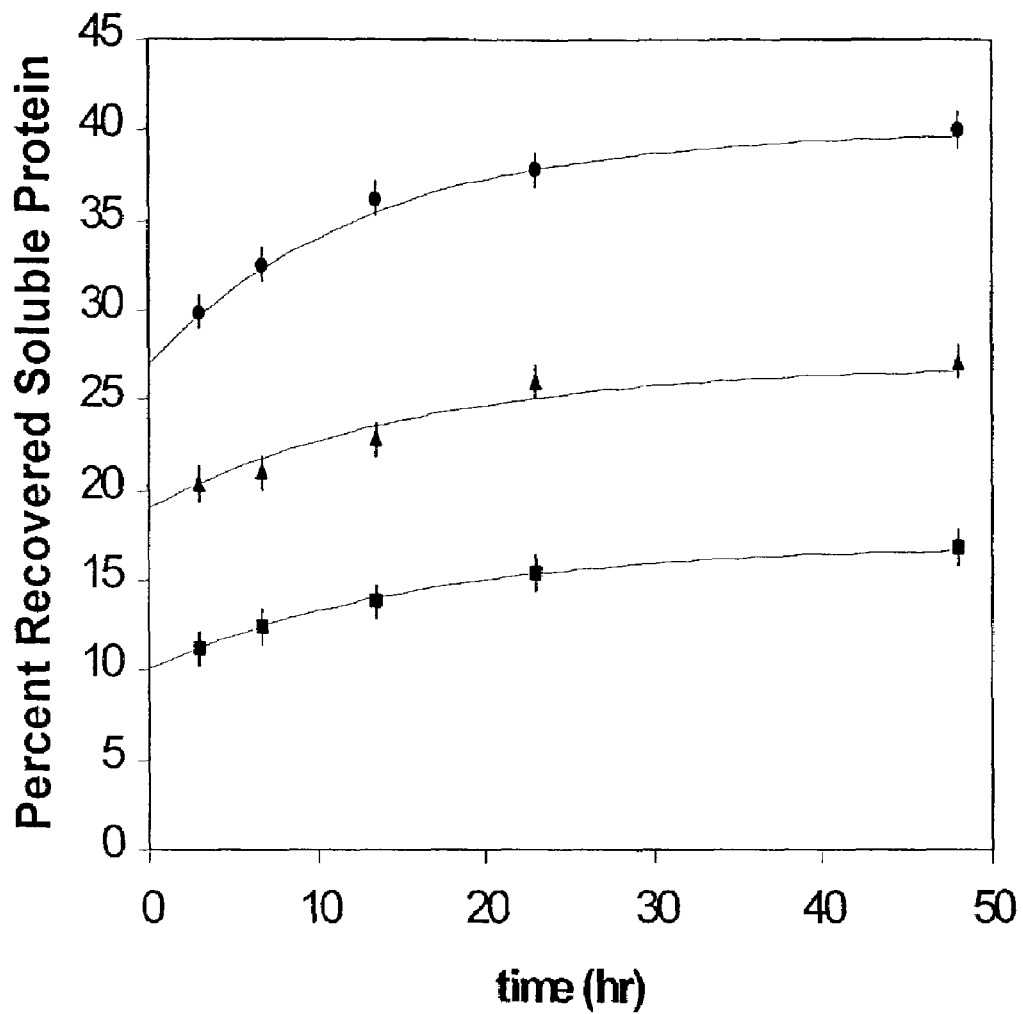
FIG. 3B shows the percent recovered soluble rhGH as a function of time under ambient atmospheric pressure. Squares (■) represent samples refolded in 0.25M GdmHCl, triangles (▲) represent samples refolded in 0.5M GdmHCl, and circles (●) represent samples refolded in 0.75M GdmHCl.

To determine whether the observed refolding yields represent equilibrium values, we investigated the effects of duration of pressure exposure on the degree of refolding measured after return to atmospheric pressure (FIGS. 3A–3B). At 0.87 mg/mL rhGH and a given concentration of GdmHCl, refolding yields reach a plateau at approximately 24 hours in samples exposed to pressure (FIG. 3A) as well as those held at atmospheric pressure (FIG. 3B). Thus, the values previously shown in FIG. 2 represent results taken after the refolding had reached a maximum for the respective conditions. The existence of the plateaus implies that a steady state (but nonequilibrium, assuming that the native state is still favored) condition is achieved within 24 hours for each GdmHCl concentration. There are, thus, undefined kinetic barriers to refolding, such as incomplete disaggregation, in samples with less than 0.75M GdmHCl.

Figure 4:
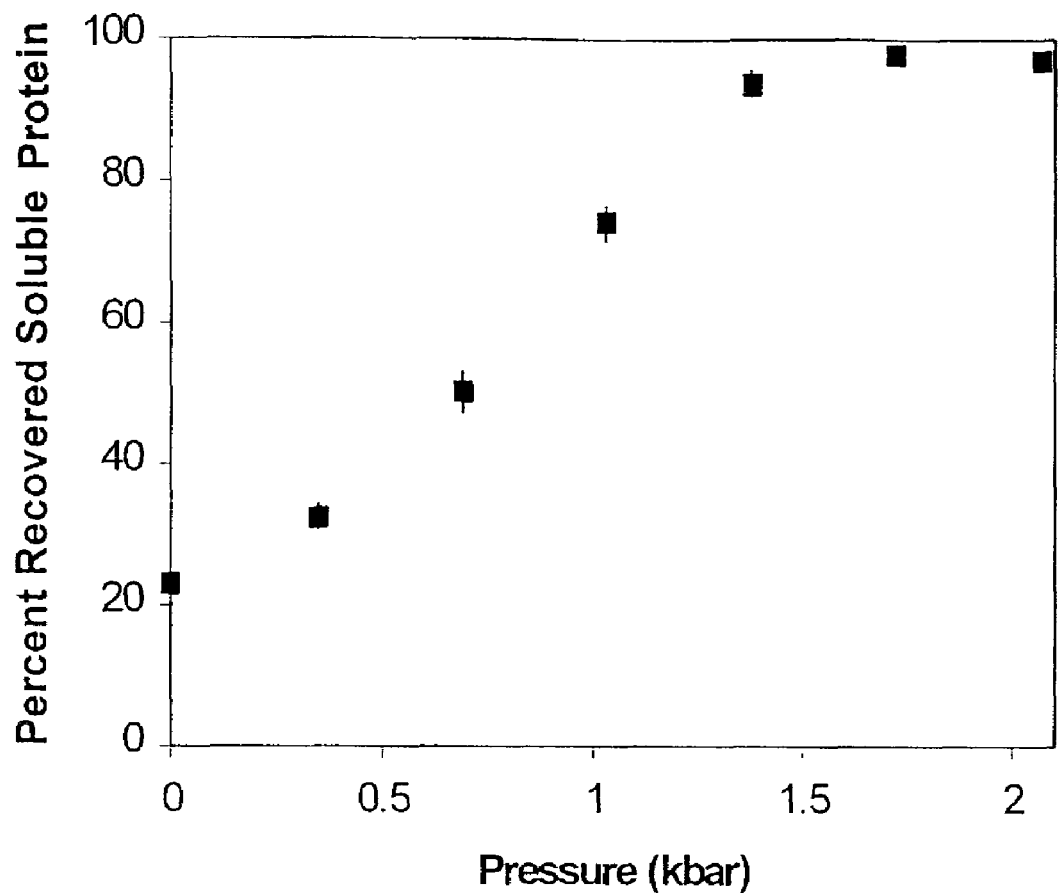
FIG. 4 is a plot of the percent recovered soluble rhGH as a function of pressure. Samples were refolded in 0.75M GdmHCl and pressurized for 24 hours at 2 kbar.

We also examined the effects of varying pressure on rhGH refolding in 0.75M GdmHCl solutions. At 0.87 mg/mL, after 24 hours of incubation at pressure and return to atmospheric pressure, recovery of soluble protein as a function of pressure increases until 100% recovery is achieved at approximately 1.75 kbar (FIG. 4).

Proteins containing cysteine can form covalent aggregates with intermolecular disulfide bonds and, potentially, non-native intramolecular disulfide bonds (i.e., "disulfide scrambling"). Clearly, proper refolding of these covalent aggregates cannot be achieved with treatment with chaotrope alone and can be much more complicated than refolding from non-covalent aggregates. Proper refolding of these proteins requires complete reduction of the protein in order to perform the solubilization step. Then, the correct disulfide bonds must be reformed via air oxidation, an oxido-shuffling system, or exposure to mixed disulfides [Rudolph, R. (1990) *Modern Methods in Protein and Nucleic Acid Research* (Tschesche, H. ed) pp. 149–172]. Most frequently, a mixture of low molecular weight thiols such as glutathione (oxidized and reduced) is employed to reshuffle disulfide bonds during refolding [Clark et al. (1998) *Biotechnology Progress* 14:47–54]. Although these conditions have been shown to be useful in attempts to refold lysozyme (whose native conformation contains four disulfides) from initially soluble, unfolded molecules, studies on lysozyme inclusion bodies have been less successful [Fischer et al. (1992) *Protein Engineering* 5:593–596].

Figure 5:
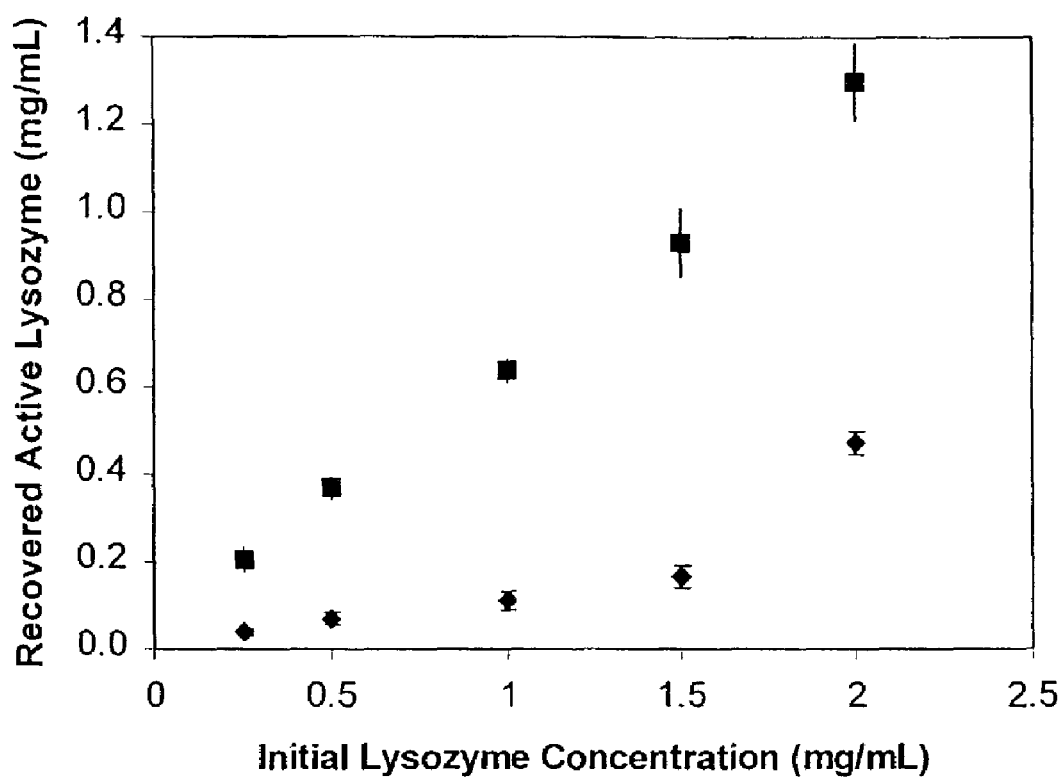
FIG. 5 is a plot of recovered active lysozyme vs. initial lysozyme concentration. Refolding buffer of 50 mM Tris (pH 8.0), 0.8 M GdmHCl, 1 mM EDTA, 5 mM GSSG, and 2 mM DTT was used. Diamonds (♦) represent atmospheric samples and squares (■) represent samples pressurized to 2 kbar for 48 hours.

Precipitates of denatured, covalently crosslinked, lysozyme were prepared by completely unfolding in the presence of 8M guanidine hydrochloride and 40 mM dithiothreitol to reduce the protein, followed by shock dilution in buffer and reoxidation. Infrared spectroscopy revealed that the precipitates had a high proportion of non-native intermolecular $\beta$-sheet structure. Aggregates were pressurized to 2 kbar for 48 hours and tested for soluble protein and catalytic activity after depressurization. Recovery of catalytic activity is a sensitive indicator of proper refolding and requires reforming of the four proper disulfides in the native conformation [P. Jolles, Ed., (1996) *Lysozymes: Model Enzymes in Biochemistry and Biology* (Birkhauser-Verlag, Boston) pp. 143–161]. Recovered activity after pressurization increased linearly with lysozyme concentration. Remarkably, at all concentrations tested up to 2 mg/mL, yields of catalytically active protein were approximately 70 percent (FIG. 5), with 100% recovery of soluble protein. No attempt was made to optimize ratios of oxidized glutathione to dithiothreitol for maximum refolding, and routine optimization improves yield. Without wishing to be bound by any particular theory, we propose that the 30% unrecoverable protein activity is the result of suboptimal redox conditions. Less than 30% recovery of activity was also noted with samples held at atmospheric pressure.

During the overexpression of recombinant protein in *E. coli*, dense, insoluble particles of aggregated protein often are formed. These structures, referred to as inclusion bodies, contain a high level of non-native intermolecular $\beta$-sheet structure, and pose a serious obstacle to efficient production of recombinant proteins. To test the applicability of high pressures to obtaining native proteins from inclusion bodies, we studied a cytoplasmic inclusion body system in *E. coli* that contains recombinant $\beta$-lactamase as a major protein component. Infrared spectroscopy of harvested and washed $\beta$-lactamase inclusion bodies documented that this system contains a large fraction of non-native intermolecular $\beta$-sheet structure. As shown in Table 1, application of 2 kbar pressure for 48 hours results in significant levels of recovered catalytic activity, even in the absence of GdmHCl. In contrast, inclusion bodies held at atmospheric pressure show no catalytic activity below 1 M GdmHCl, consistent with earlier published results. In addition, at atmospheric pressure, GdmHCl at concentrations below IM has little effect on protein solubility.

Surprisingly, application of pressure in the absence of GdmHCl served not only to recover $\beta$-lactamase activity, but also to purify the protein. At higher GdmHCl concentrations, the total amount of soluble protein increases, although the amount of soluble $\beta$-lactamase and its recovered activity remain roughly constant.

We have concluded that pressure provides a powerful tool for obtaining native protein molecules from soluble and insoluble aggregates. Success with the methods of the present invention is not dependent on the identity of the protein; these methods can be successfully applied to virtually any protein aggregate or inclusion body protein. This process allows proteins to be refolded from such aggregates at concentrations orders of magnitude greater than reported previously, and at yields approaching 100%. In fact, recovery of both rhGH and lysozyme exhibited independence of protein concentration in the ranges studied. All previous refolding studies report strong negative dependence of recovery of native protein on protein concentration, even when concentrations were very low (e.g., usually 1–50 µg/mL) [Valax and Georgiou (1993) *Biotechnology Progress* 9:539–547; Rudolph and Lilie (1996) *The FASEB Journal* 10:49–56]. For example, a study on lysozyme recovery from inclusion bodies required protein concentrations of less than 40 µg/mL [Fischer et al. (1992) *Protein Engineering* 5:593–596], while another study on refolding from soluble, denatured lysozyme reported that recovery of activity dropped from ca. 95% at 50 µg/mL to ca. 25% at 1 mg/mL [Clark et al. (1998) *Biotechnology Progress* 14:47–54]. Refolding from a denatured (but not aggregated) protein at concentrations above 1 mg/mL has been achieved [Hevehan and Clark (1997) *Biotechnology and Bioengineering* 54:221–230; Maeda et al. (1996) *Protein Engineering* 9:95–100], but such results have not yet been reported when refolding proteins recovered from aggregates.

Recombinant or other proteins can be produced and isolated by any of a number of techniques well-known to the art. Once isolated, the proteins can be solubilized by a variety of prior art techniques, or a combination of pressure and chaotropic agent (and optionally, also a reducing agent). Renaturation to a biologically active protein conformation proceeds under conditions of elevated pressure (especially from about 0.5 kbar to about 3 kbar), and optionally in the presence of a non-denaturing (at ambient atmospheric pressures) concentration of chaotropic agent (for example, about 0 to about 2 M GdmHCl) and/or redox reagents (for example dithiothreitol and oxidized glutathione). Practice of the methods of the present invention allows recovery of properly refolded (native conformation) protein with full biological activity at yields approaching 100%. Because the solubilized denatured protein can be properly refolded at higher protein concentrations than prior art methods allowed, the present invention has environmental and economical advantages associated with lower volumes of material processed and higher yield of properly folded, biologically active protein.

Monoclonal or polyclonal antibodies, preferably monoclonal, specifically reacting with a particular protein of interest may be made by methods known in the art. See, e.g., Harlow and Lane (1988) *Antibodies: A Laboratory Manual*, Cold Spring Harbor Laboratories; Goding (1986) *Monoclonal Antibodies: Principles and Practice*, 2d ed., Academic Press, New York; and Ausubel et al. (1987) supra.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Ausubel et al. (1992) *Current Protocols in Molecular Biology*, Green/Wiley, New York, N.Y.; Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol* 218, Part I; Wu (ed.) (1979) *Meth. Enzymol*. 68; Wu et al. (eds.) (1983) *Meth. Enzymol*. 100 and 101; Grossman and Moldave (eds.) *Meth. Enzymol*. 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Methods in Molecular Biology*; Glover (ed.) (1985) *DNA Cloning* Vol. I and II, IRL Press, Oxford, UK; Hames and Higgins (eds.) (1985) *Nucleic Acid Hybridization*, IRL Press, Oxford, UK; Setlow and Hollaender (1979) *Genetic Engineering: Principles and Methods*, Vols. 1–4, Plenum Press, New York; and Ausubel et al. (1992) *Current Protocols in Molecular Biology*, Greene/Wiley, New York, N.Y. Abbreviations and nomenclature, where employed, are deemed standard in the field and commonly used in professional journals such as those cited herein.

The following examples are provided for illustrative purposes, and are not intended to limit the scope of the invention as claimed herein. Any variations in the exemplified articles which occur to the skilled artisan are intended to fall within the scope of the present invention.

All references cited in the present application are incorporated by reference herein to the extent that there is no inconsistency with the present disclosure.

EXAMPLES

Example 1

Materials

Recombinant human growth hormone lyophilized in ammonium bicarbonate was obtained from Genentech Inc., South San Francisco, Calif. Hen egg white lysozyme, three times crystallized, dialyzed and lyophilized (Cat. #L-6876, lot #65H7025), EDTA (Cat. #E-5134), sodium azide (Cat. #S-8032), and guanidine chloride (Cat. #G-4505), were obtained from Sigma Chemicals (St. Louis, Mo.). Dithiothreitol (DTT) (Cat. #D-5545), and Micrococcus lysodeikticus cells (Cat. #M-3770), were also obtained from Sigma. Tris base was purchased from Fisher Scientific (Pittsburgh, Pa.) (Cat. #BP152–500). Sodium citrate was purchased from J. T. Baker Chemical Co. (Phillipsburg, N.J.) (Cat. #3643-1).

Example 2

Analytical Techniques

Fourier Transform Infrared Spectroscopy (FTIR) was used to determine the secondary structure of growth hormone aggregates in solution. All spectra were collected on a Nicolet Magna model 550 spectrometer equipped with a dTGS detector (Nicolet Instrument Corp., Madison, Wis.). A 256-scan interferogram was acquired in single-beam mode with a 4 cm$^{-1}$ resolution. Aggregate slurries were placed in an adjustable path-length IR cell set at 8 microns. The same cell was used to collect a buffer blank (the buffer used for the blank was identical to the buffer in the aggregate slurry). Buffer and water vapor contributions were subtracted from the spectrum using the Nicolet software. Second derivative analysis was used for peak narrowing and resolution. Contributions from the second derivative of the water vapor spectrum were also subtracted from the spectrum. A seven-point smoothing was used to remove white noise, and baseline correction was performed over the amide I region. Finally, spectra were normalized by their total area over the amide I region.

FTIR can also be applied to the analysis of the secondary structures of other proteins.

Circular dichroism (CD) spectroscopy (Aviv Model 62DS) is used to analyze the secondary and tertiary structure of proteins. Far UV wavelength ranges (180 nm to 250 nm) were scanned for secondary structural elements, and near UV wavelength ranges (250 nm to 320 nm) were scanned for tertiary structure. In the far UV scan, a protein concentration of 0.1 mg/mL and a path length of 0.1 cm, and in the near UV scan, a protein concentration of 0.9 mg/mL and a path length of 1 cm were used. Protein-free buffer was used as a blank.

Concentrations of soluble rhGH are determined by UV spectroscopy with extinction coefficients of 18,890 (cm mol/l)-1 at 278 nm (19) on a Hewlett Packard 8452A diode array spectrophotometer (Hewlett Packard, Palo Alto, Calif.). Insoluble aggregates are removed by centrifugation (13,000 g, room temperature) for 15 minutes. Contributions due to soluble aggregates are subtracted from the signal as previously reported [Leach and Scheraga (1960) *Journal of the American Chemical Society* 82:4790–4792].

Concentrations of both denatured and renatured lysozyme were determined with UV spectroscopy. Samples were centrifuged (13,000 g, room temperature) for 15 minutes to eliminate insoluble aggregates. Extinction coefficients for denatured and native lysozyme are 2.37 and 2.63 (cm mg/mL)$^{-1}$ respectively [Clark et al. (1998) *Biotechnology Progress* 14:47–54]. Contributions due to soluble aggregates were subtracted from the signal as previously reported [Leach and Scheraga (1960) *Journal of the American Chemical Society* 82:4790–4792].

Total protein concentrations are measured using the BCA assay method (Pierce Chemical Co., Rockford, Ill.) and bovine serum albumin as the standard.

Lysozyme catalytic activity was measured by a method similar to the one described by Jolles [Jolles, P. (1962) *Methods in Enzymology* 5:137–140]. 0.25 mg/mL of *M. lysodeikticus* cells were suspended in 67 mM potassium phosphate buffer, pH 6.2. All samples were diluted in Tris buffer (pH 8.0, 1 mM EDTA) to a concentration between 0.05 and 0.25 mg/mL. 10 µl of the diluted samples were then mixed into 990 µl of cell suspension to initiate the reaction. Absorbance of the sample was measured at 450 nm for 90 seconds. Slopes of an absorbance vs. time plot were calculated on points between 30 and 90 seconds. Lysozyme concentrations were calculated based on the specific activity of fully native lysozyme.

The enzymatic activity of β-lactamase is measured using penicillin G as substrate in a spectrophotometric method described by Walcy, S.g. (1974) *Biochem. J.* 139:789–790.

HPLC analysis of soluble protein fractions was performed on a Beckman Gold HPLC system (Beckrman Instruments Inc., Fullerton, Calif.), equipped with a Tosohaas 2000 SW size exclusion column and a 0.2 µm prefilter. A mobile phase of 10 mM sodium citrate buffer, pH 6.0 (rhGH samples) or 1.2 M KCl (β-lactamase samples) at 0.8 mL/min was used, and 20 ml samples were injected with an autosampler. Protein elution was monitored by absorbance at 214 nm. To analyze the amount of b-lactamase remaining in the insoluble fraction after pressurization, the insoluble pellets were first dissolved in 4M GdmHCl, 4 mM dithiothreitol, and then injected on the column.

Example 3

High Pressure Treatment

Pressure was generated using high-pressure nitrogen (400 bar) connected to 10-fold hydraulic intensifier equipment (High Pressure Equipment Company, Erie, Pa.). Time to reach the desired pressure was typically 10 min. The nitrogen input is connected to a 10-fold hydraulic intensifier, which is connected to a 2-liter cloverleaf reactor rated to 30,000 psi (2 kbar). For higher pressures, equipment is modified for higher ratings. Samples were prepared in heat-sealed bulbs of SAMCO® plastic transfer pipets (Fisher Scientific, Pittsburgh, Pa.) and placed in a to a 2 liter clover leaf reactor rated to 2,000 bar and filled with water. Samples were slowly pressurized (over 10 minutes) to the final desired pressure. Pressurization-induced heating was minimized. The depressurization rate was approximately 10 bar per minute.

Example 4

Recombinant Human Growth Hormone

Human growth hormone (lyophilized in ammonium bicarbonate) was dissolved at a concentration of 2 mg/mL in 10 mM sodium citrate (pH 6.0), 1 mM EDTA and 0.1% sodium azide as a bacteriocide.

Aggregates of rhGH were produced rotating 10 mL of rhGH (Genentech, South San Francisco, Calif.) solution in a 50 mL Falcon tube on a cell suspender at 8 RPM for 48 hrs at room temperature. Samples were prepared in 10 mM sodium citrate buffer (1 mM EDTA, 0.1% sodium azide, pH 6.0) at a concentration of 2 mg/mL rhGH. Alternatively, samples were aggregated in the presence of 0.75 M guanidine hydrochloride. Prior to pressurization, samples containing aggregated rhGH were diluted to 1 mg/mL protein with appropriate GdmHCl solutions in buffer to yield desired refolding conditions.

In a typical experiment, 0.65 mL aggregated growth hormone solution and 0.65 mL 1.5 M guanidine hydrochloride in sodium citrate buffer (as specified above) were placed in the bulb of a 1.3 mL plastic transfer pipet. The pipet was heat-sealed and placed in the pressure chamber. The vessel was pressurized to 30,000 psi for 24 hours. Then the pressure was released at a rate of 3000 psi per 15 minutes. The samples were centrifuged for 15 minutes to sediment any remaining insoluble aggregates. Soluble protein concentration by measured as a function of absorbance at 278 nm, correcting for soluble aggregates by subtracting a baseline created at wavelengths between 350 nm and 500 nm and extrapolated to 278 nm.

Example 5

Lysozyme

Lysozyme was aggregated by first unfolding and reducing 40 mg/mL lysozyme in 8M GdmCl and 40 mM DTT prepared in 50 mM Tris (pH 8.0), 1 mM EDTA, 0.1% sodium azide. Samples were shock-diluted between 10 and 40 fold with 50 mM tris buffer (1 mM EDTA, pH 8.0) to induce aggregation. Tris buffer containing dithiothreitol (DTT), oxidized glutathione (GSSG), and GdmHCl was then added to yield a refolding buffer of 50 mM Tris (pH 8.0), 0.8M GdmCl, 5 mM GSSG, 2 mM DTT.

Example 6

β-Lactamase

E. coli strain RB791 cells transfected with pGB 1 were grown as described previously (Valax, P., and Georgiou, G., in Biocatalyst Design for Stability & Specificity, M. Himmel and G. Georgiou, eds., American Chemical Society, Washington, D.C., 1993, pp 126–139). β-lactamase synthesis was induced by the addition of 0.1 mM isopropyl-β-D-thiogalactoside at an optical density between 0.35 and 0.4 (600 nm). Cell cultures were grown overnight.

Upon completion of cell growth, cells were centrifuged (6000 g, 4° C.) and resuspended in washing buffer (50 mM Tris-HCl, pH 8.0, 0.2% lysozyme). After 30 min. incubation, cells were lysed with a homogenizer (Vertishear 2000) (Virtis, Gardiner, N.Y.) and centrifuged as above. The pellet was washed and centrifuged again. The pellet was then resuspended in washing buffer and incubated at room temperature for 20 minutes. Then, 2% sodium deoxycholate was added and mixed at room temperature for an additional 20 minutes prior to final centrifugation to yield purified inclusion bodies.

TABLE 1

Recovery of β-lactamase from cytoplasmic inclusion bodies produced in E. coli RB791 (pGB1) as a function of [GdmHCl]. Purified inclusion bodies (32) were held at 37° C., 2 kbar for 48 hours before analysis.

| [GdmHCl] (M) | Activity [Enzymatic activity of β-lactamase was determined spectroscopically using penicillin G as a substrate (Waley, S.G. (1974) Biochem. J. 139:789–790] (Units/mg soluble protein) (standard deviation) | Total Soluble Protein (mg/mL)[a] | Percent β-lactamase recovered in soluble fraction[b] |
|---|---|---|---|
| 0 | 2200 (400) | 0.10 | 85 |
| 0.3 | 2000 (330) | 0.12 | 85 |
| 0.6 | 1200 (200) | 0.20 | 85 |
| 0.9 | 700 (200) | 0.22 | 85 |
| 1.2 | 400 (100) | 0.43 | 84 |

[a]Total soluble protein by total protein assay relative to BSA standard [Protein concentrations reported were measured with the BCA total protein assay distributed by Pierce. Standard concentrations of bovine serum albumin were used to calibrate the method.]
[b]Recovery of soluble β-lactamase based on size exclusion chromatography [HPLC analysis of soluble protein fractions was performed on a Beckman Gold HPLC system, equipped with a Tosohaas 2000 SW size exclusion column and a 0.2 mm prefilter. A mobile phase of 10 mM sodium citrate buffer, pH 6.0 (rhGH samples) or 1.2 M KCl (β-lactamase samples) at 0.8 mL/min was used, and 20 ml samples were injected with an autosampler. Protein elution was monitored by absorbance at 214 nm. To analyze the amount of β-lactamase remaining in the insoluble fraction after pressurization, the insoluble pellets were first dissolved in 4M GdmHCl, 4 mM dithiothreitol, and then injected on the column.]. Percent recovery is determined as 100 × (height of β- lactamase peak in the soluble fraction, divided by the sum of the peak heights of β-lactamase in the soluble fraction and in the remaining insoluble pellet). All peak heights were corrected appropriately for dilution.

What is claimed is:

1. A method for producing disaggregated biologically active protein from a mixture comprising aggregated protein comprising the steps of:

(a) adjusting total protein concentration in the aggregate mixture to from about 0.01 mg/mL to about 500 mg/mL; then (b) increasing the pressure on the aggregate mixture to from about 0.25 kbar to about 12 kbar for a time and temperature sufficient for disaggregation of the protein; then (c) incubating the mixture under pressure in the range from about 0.25 kbar to about 3.3 kbar; then (d) reducing the pressure to atmospheric pressure, whereby protein in the mixture remains disaggregated and biological activity is retained;

wherein said pressure is reduced at a controlled depressurization rate.

2. The method of claim 1, wherein said controlled depressurization rate is from about 10 bar/minute to about 13.3 bar/minute.

3. The method of claim 2, wherein said controlled depressurization rate is about 10 bar/minute.

4. The method of claim 2, wherein said controlled depressurization rate is about 13.3 bar/minute.

5. The method of claim 1, wherein during the incubation step (c), the protein concentration is from about 1 to about 100 mg/mL.

6. The method of claim 2, wherein during the incubation step (c), the protein concentration is from about 1 to about 100 mg/mL.

7. The method of claim 3, wherein during the incubation step (c), the protein concentration is from about 1 to about 100 mg/mL.

8. The method of claim 4, wherein during the incubation step (c), the protein concentration is from about 1 to about 100 mg/mL.

9. The method of claim 1, wherein during the incubation step (c), the protein concentration is from about 1 to about 20 mg/mL.

10. The method of claim 2, wherein during the incubation step (c), the protein concentration is from about 1 to about 20 mg/mL.

11. The method of claim 3, wherein during the incubation step (c), the protein concentration is from about 1 to about 20 mg/mL.

12. The method of claim 4, wherein during the incubation step (c), the protein concentration is from about 1 to about 20 mg/mL.

13. The method of claim 1, wherein, prior to step (a), the aggregated protein is treated with a reducing agent.

14. The method of claim 1, further comprising adding, prior to step (b), a chaotropic agent at a concentration up to about 8 M.

15. The method of claim 1, further comprising adding, prior to step (b), a chaotropic agent at a concentration up to about 1.0 M.

16. The method of claim 15, wherein the chaotropic agent is guanidinium hydrochloride.

17. The method of claim 1, wherein after step (c), the concentration of the chaotropic agent is decreased to less than about 0.1 M.

* * * * *

UNITED STATES PATENT AND TRADEMARK OFFICE
CERTIFICATE OF CORRECTION

PATENT NO.        : 7,064,192 B2
APPLICATION NO.   : 10/292692
DATED             : June 20, 2006
INVENTOR(S)       : Theodore W. Randolph et al.

It is certified that error appears in the above-identified patent and that said Letters Patent is hereby corrected as shown below:

On Title Page, first column, Item (62), Related U.S. Application Data, please replace "Division of application No. 09/350,327, filed on Jul. 9, 1999, now Pat No. 6,489,450." with --Continuation of application No. 09/350,327, filed on Jul. 9, 1999, now Pat. No. 6,489,450.--

Signed and Sealed this

Twelfth Day of September, 2006

JON W. DUDAS
*Director of the United States Patent and Trademark Office*